United States Patent [19]

Ton et al.

[11] Patent Number: 5,746,769
[45] Date of Patent: May 5, 1998

[54] ENDOLUMINAL COIL DELIVERY SYSTEM HAVING A MECHANICAL RELEASE MECHANISM

[75] Inventors: Dai T. Ton, San Jose; Julian N. Nikolchev, Portola Valley, both of Calif.

[73] Assignee: Conceptus, Inc., San Carlos, Calif.

[21] Appl. No.: 735,348

[22] Filed: Oct. 22, 1996

Related U.S. Application Data

[63] Continuation of Ser. No. 525,485, Sep. 8, 1995, Pat. No. 5,601,600.

[51] Int. Cl.⁶ ............................................ A61B 17/28
[52] U.S. Cl. ........................ 606/206; 606/191; 606/198
[58] Field of Search ........................ 606/191, 206, 606/198, 108, 200, 195; 623/1, 12

[56] References Cited

U.S. PATENT DOCUMENTS

| | | | |
|---|---|---|---|
| 3,868,956 | 3/1975 | Alfidi et al. | 128/345 |
| 4,994,069 | 2/1991 | Ritchart et al. | 606/191 |
| 5,108,407 | 4/1992 | Geremia et al. | 606/108 |
| 5,122,136 | 6/1992 | Guglielmi et al. | 606/32 |
| 5,234,437 | 8/1993 | Sepetka | 606/108 |
| 5,250,071 | 10/1993 | Palermo | 606/198 |
| 5,261,916 | 11/1993 | Engelson | 606/108 |
| 5,304,195 | 4/1994 | Twyford, Jr. et al. | 606/191 |
| 5,312,415 | 5/1994 | Palermo | 606/191 |
| 5,354,295 | 10/1994 | Guglielmi et al. | 606/32 |

FOREIGN PATENT DOCUMENTS

| | | | |
|---|---|---|---|
| 7810696 | 4/1980 | European Pat. Off. | A61F 5/46 |
| 0 010 812 A1 | 5/1980 | European Pat. Off. | A61F 5/47 |
| 2211095 | 6/1989 | United Kingdom | A61F 5/47 |

OTHER PUBLICATIONS

Gupta, D.N. et al., "Antifertility Effect of an Intrafallopian Tubal Copper Device," *Indian J. Exp. Biol.*, vol. 14, pp. 316–319, May, 1976.

Ross, P.L. et al., "Transcatheter Tubal Sterilization in Rabbits," *Investigative Radiology*, vol. 29, No. 5, pp. 570–573, 1994.

*Primary Examiner*—Michael Buiz
*Assistant Examiner*—Kevin Truong
*Attorney, Agent, or Firm*—Townsend and Townsend and Crew LLP

[57] ABSTRACT

The invention provides endoluminal coil delivery systems and methods for positioning a coil within a body lumen. In particular, the device uses a mechanical latch in the form of jaws to positively engage the coil during positioning. The coil may be restrained in a straight configuration from within the coil, using an internal coilwire, or from outside using a catheter. Thus, the mechanism for releasing the coil to form its relaxed convoluted shape is separate from the mechanism for disengaging the coil from the delivery system. The use of an internal core wire allows a coil having a helical outer surface to be torqued against a fallopian tube or other body lumen wall, thereby firmly anchoring the coil in the target position prior to disengaging the delivery system.

29 Claims, 2 Drawing Sheets

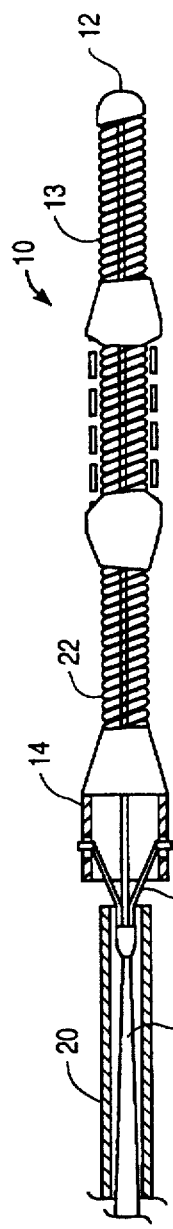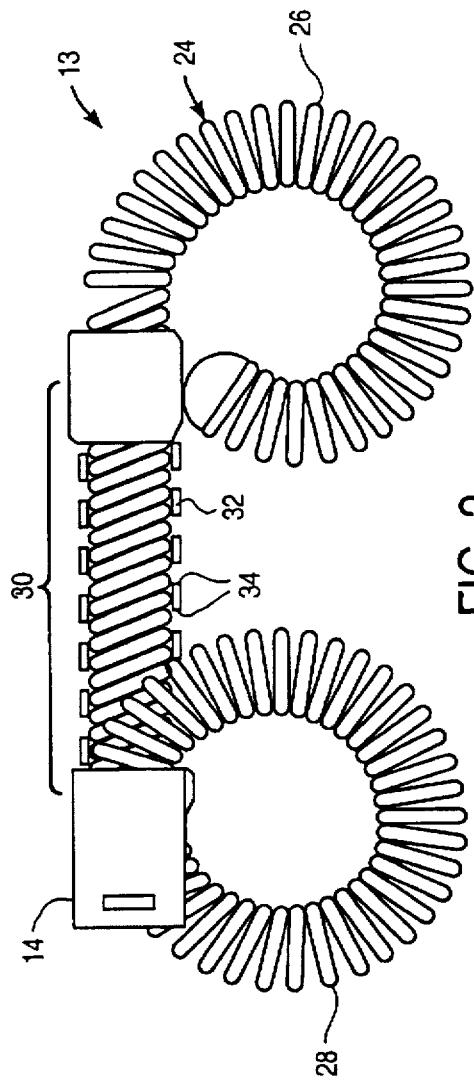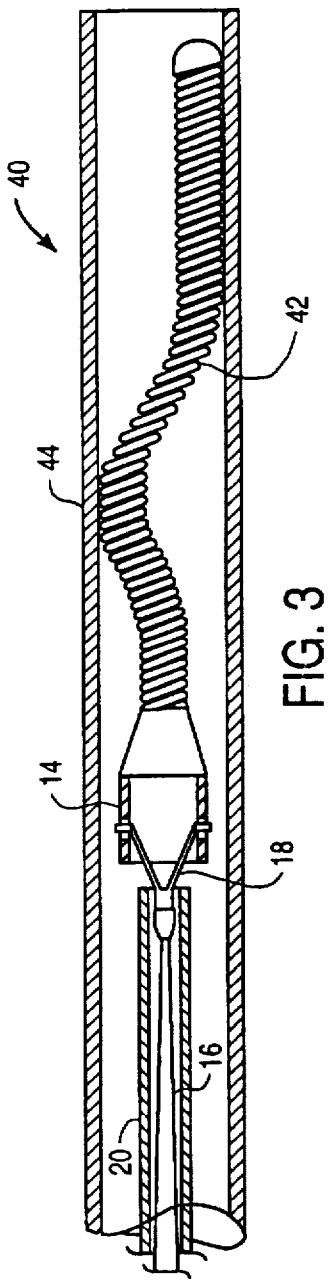

ENDOLUMINAL COIL DELIVERY SYSTEM HAVING A MECHANICAL RELEASE MECHANISM

This is a Continuation of application No. 08/525,485 filed Sep. 8, 1995 now U.S. Pat. No. 5,601,600 the disclosure of which is incorporated by reference.

BACKGROUND OF THE INVENTION

1. Field of the Invention

The present invention relates generally to therapeutic placement of endoluminal coils, and more particularly to a coil delivery system having a mechanical latch.

Endoluminal coils have a wide variety of existing and proposed therapeutic uses. Existing therapies often make use of endovascular coils, for example, in the treatment of vascular aneurysms. Aneurysms are the result of abnormal dilation of a blood vessel, usually resulting from disease and/or genetic predisposition, which can weaken the arterial wall and allow it to expand. In vasoocclusion coil therapy, a number of coils are typically placed within the aneurysm to occlude the site by posing a physical barrier to blood flow, and by promoting the formation of thrombus.

The use of coils has recently been proposed to provide contraception or permanent sterilization. Contraceptive intrafallopian coils can be anchored within the isthmus of the fallopian tube to occlude the tube and prevent conception. Anchoring of intrafallopian coils is enhanced by providing a helical outer surface, while the efficacy of an intrafallopian coil as a contraceptive is improved by including copper with the coil. Exemplary contraceptive intrafallopian coils are described in copending U.S. patent application Ser. Nos. 08/474,779 and 08/475,252 (Attorney Docket Nos. 16355-24 and 16355-25), the full disclosures of which are hereby incorporated by reference.

Coils have typically been placed at the desired site within body lumens using a catheter and a pusher. The catheter is first positioned near the site, typically using a guidewire under fluoroscopy, ultrasound, or the like. Once the site has been reached, the guidewire is removed. The coil is then inserted into the proximal end of the catheter lumen and advanced through the catheter using a pusher. Pushers are typically simple wires having a distal end that is adapted to advance the coil. When the coil reaches the distal end of the catheter, it is discharged from the catheter by advancing the pusher, or alternatively by axially restraining the pusher and retracting the catheter from around the coil. When using a standard catheter and pusher delivery system, coils are simultaneously decoupled from the delivery catheter and released from a straight configuration.

Endoluminal coils are generally resilient structures which are biased to form bent secondary shapes when released. The coils are restrained by the catheter wall in a relatively straight configuration, allowing the resilient coils to be advanced along narrow, torturous luminal paths. As the coil advances out the distal end of the catheter, it tries to assume its relaxed, bent shape, which is typically larger in cross-section than the body lumen in which the coil is being positioned. The resilient force of the released coil against the lumen wall anchors the coil within the lumen.

Although the release of endoluminal coils using catheters and pushers has proven effective, the technique suffers from a number of undesirable limitations. First, the position of the coil at the site cannot be controlled to a fine degree of accuracy. While the coil is restrained in a straight configuration, it extends along a considerable length of the body lumen. As the coil is released, it will anchor against the lumen wall somewhere along this length. However, the coil in its relaxed state will extend along a much shorter length of lumen, and the final location of the released, convoluted coil along the body lumen is difficult to predict. Second, once the coil has left the catheter, it is difficult to reposition or retrieve the coil. Third, the use of a catheter and pusher release technique for anchoring of helically surfaced coils within body lumens is problematic. The catheter wall prevents the helical shape from seating while the coil is in the straightened configuration, and the pusher/coil interface does not allow torquing of the coil to seat the helical shape against the lumen wall.

For these reasons, it is desirable to provide effective, reliable endoluminal delivery systems and methods for their use. It would be particularly desirable if such delivery systems promoted the precise positioning of a coil within a body lumen, preferably by providing separate coil coupling and release mechanisms. Ideally, such systems and methods would allow a retrieval of a partially anchored coil from within the body lumen. It would be further desirable if coil delivery systems were provided which allowed torquing of a helically shaped intrafallopian coil to anchor the coil against the fallopian tube.

2. Description of the Related Art

U.S. Pat. No. 5,250,071 describes an embolic coil delivery device using a series of interlocking clasps pinned together with a control wire. U.S. Pat. Nos. 5,261,916 and 5,304,195 describe detachable pusher-vasoocclusive coil assemblies having interlocking ball couplings. Release of each of these coils is accomplished by advancing the coupling beyond the end of a restraining catheter.

U.S. Pat. No. 5,234,437 describes a detachable pusher vasoocclusion coil assembly having a threaded coupling which provides release of the coil on rotation of the pusher. U.S. Pat. No. 5,312,415 describes a similar pusher/coil coupling.

U.S. Pat. Nos. 5,122,136 and 5,354,295 describe electrolytically detachable guidewire tips for the endovascular formation of thrombus. U.S. Pat. No. 5,108,407 describes an embolic coil pusher apparatus having a heat releasable adhesive bond which is decoupled using laser energy transmitted along a fiber optic cable. U.S. Pat. Nos. 3,868,956 and 4,994,069 are also generally relevant.

The experimental use of a stainless steel intrafallopian device is described in "Transcatheter Tubal Sterilization in Rabbits," Penny L. Ross, RT 29 *Investigative Radiology*, pp. 570–573 (1994). The experimental use of an electrolytically pure copper wire as a surgical contraceptive intrafallopian device in rats was described in "Antifertility Effect of an Intrafallopian Tubal Copper Device," D.N. Gupta, 14 *Indian Journal of Experimental Biology*, pp. 316–319 (May 1976).

U.K. Patent Application Pub. No. 2,211,095 describes a uterine screw plug for blocking the fallopian tube. European Patent Application Pub. No. 0,010,812 describes a device for placement in the oviducts having enlargements at either end for anchoring the device. The same device appears to be described in Netherlands Patent No. 7,810,696.

SUMMARY OF THE INVENTION

In a first aspect, the present invention provides an endoluminal coil delivery system comprising an endoluminal coil and a first elongate body. Jaws are affixed to either the coil or the first body, and engage the other. A second elongate body articulates relative to the first body to manipulate the jaws and release the coil. As used herein, "jaws" means a reciprocatable grasping structure, including both compressive grasping structures and structures which expand outward to engage. Preferably, the jaws are resiliently biased toward an engaged position, thereby providing a positive attachment for positioning of the coil, and also providing a positive tactile feedback to the attending physician. In a particularly preferred embodiment, the jaws are biased outward against the coil, while the first body is slidably disposed within the second body. Thus, axially sliding the second body down the first body collapses the jaws and releases the coil. This simple, positive coupling arrangement provides an endoluminal coil delivery system having a small, smooth outer coupling surface which is particularly advantageous for maneuvering in small, tortuous body lumens.

In another aspect, the present invention provides an improved endoluminal coil of the type having a resilient body biased to form a bent secondary shape which is restrainable in a straight configuration. The improvement comprises a fitting disposed on the coil, the fitting having a plurality of axially opposed detents for engaging jaws on a delivery device. The detents may take the form of protuberances, but will preferably comprise indentations or cavities in the fitting which mate with pins located on the delivery device jaws. As used herein, "axially opposed" means the detents are disposed about the axis of the restrained coil so as to allow opposing jaws to firmly restrain the coil relative to the delivery device. Preferably, the detents are accessible from within a jaw receiving cavity of the fitting, thereby providing positive rotational connection for an outwardly biased set of jaws. Ideally, the cavity is in communication with a lumen of the coil, thereby providing access for a corewire to releasably restrain the coil in a straight configuration during insertion and positioning. This internally restrained coil provides a particularly small outer diameter, and also leaves the outer surface of the coil exposed to the body lumen to allow engagement of any additional attachment mechanisms prior to releasing the coil. For example, a coil having a helical outer shape can be torqued against the body lumen wall while the corewire restrains the coil in a straight configuration.

In yet another aspect, the present invention provides an intrafallopian contraceptive delivery system comprising a coil with a corewire disposed within the coil, the corewire restraining the coil in a straight configuration. An elongate body extends proximally from the corewire, while a release tube is slidably disposed over the body proximally of the coil. The body is mechanically latched to the coil so that rotation of the corewire transmits torque to the coil. Conveniently, axially sliding the release tube relative to the body unlatches the coil. Preferably, the coil includes a helical outer surface to promote retention of the coil within the fallopian tube. Ideally, the coil includes a proximal fitting and the body includes jaws which engage the fitting to couple the corewire to the coil.

In a still further aspect, the present invention provides an intrafallopian contraceptive delivery system comprising a coil and an elongate body extending proximally of the coil. A release tube is slidably disposed over the body, and a tubular structure is slidably disposed over the coil to restrain the coil in a straight configuration. The body is mechanically latched to the coil, and sliding the release tube axially relative to the body unlatches the coil.

A method according to the present invention comprises inserting a coil into a body lumen while the coil is engaged by a set of jaws disposed near the end of a first elongate body. The coil is positioned within the lumen at a target location and then disengaged by manipulating the jaws with a second elongate body. Optionally, the coil is restrained in a straight configuration by inserting a corewire within a lumen of the coil, and released by withdrawing the corewire relative to the second body. In some embodiments of the present method, the coil is anchored at the target location by torquing the first body to engage an outer helical surface of the coil against a wall of the body lumen. Alternatively, the coil is anchored at the target location prior to disengaging the jaws by releasing the coil, thereby allowing the coil to form its bent secondary shape while still coupled to the body. Hence, if the initial position of the coil is improper, the coil may be repositioned easily.

BRIEF DESCRIPTION OF THE DRAWINGS

FIG. 1 illustrates a first embodiment of an endoluminal coil delivery system according to the principles of the present invention.

FIG. 2 illustrates an endoluminal coil for use with the delivery system of FIG. 1.

FIG. 3 illustrates an alternative embodiment of an endoluminal coil delivery system according to the present invention.

DETAILED DESCRIPTION OF THE SPECIFIC EMBODIMENT

Figure 4A:
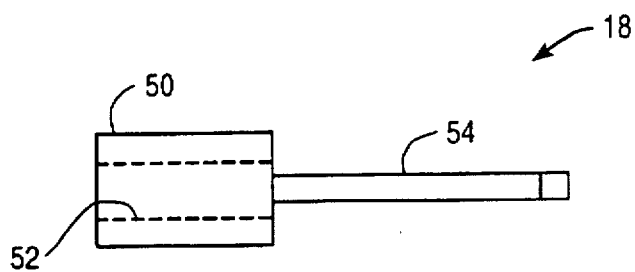
FIGS. 4A-4C illustrate a set of releasable jaws for use in the endoluminal delivery systems of FIGS. 1 and 3.

The endoluminal coils, delivery systems, and methods of the present invention will find use for the precise positioning of vasoocclusion coils for the treatment of aneurysms and other diseases. The devices and methods of the present invention are particularly well suited for the transcervical introduction of contraceptive intrafallopian devices, such as those described in copending U.S. patent application Ser. Nos. 08/474,779 and 08/475,252 (Attorney Docket Nos. 16355-24and 16355-25), the full disclosures of which have previously been incorporated herein by reference. As more fully explained in those applications, retention of an intrafallopian device within the fallopian tube is promoted by placement of a distal anchor beyond the narrowest section of the fallopian tube, referred to as the isthmus, and placement of a proximal anchor proximally of the isthmus. Optionally, retention is further promoted by providing an isthmus traversing region having a helical outer shape, preferably comprising a ribbon wound over the body of the intrafallopian device. Ideally, the ribbon includes at least one sharp outer corner, allowing the intrafallopian device to be torqued against the tubal wall, thereby anchoring the sharp corner of the ribbon in the wall of the fallopian tube.

Referring now to FIG. 1, a preferred embodiment of an endoluminal coil delivery system generally has a proximal end 11 and a distal end 12. A resilient coil 13 is disposed at the distal end of delivery system 10, and includes a proximal fitting 14. An elongate body 16 extends proximally from coil 13, and includes a set of jaws 18 which engage the proximal fitting 14 of coil 13. A release tube 20 is slidably disposed over body 16.

A corewire 22 extends distally from body 16, passing through fitting 14 and into a coil lumen. Corewire 22 restrains the coil in a straight configuration so long as jaws 18 are engaged with fitting 14. Alternatively, corewire 22 is slidably disposed within body 16, allowing the disengagement of the body from the coil to be a completely separate mechanism from the release of coil 13 from the straight configuration.

Generally, body 16 and corewire 22 are formed as a unit from a high strength biocompatible alloy, preferably including stainless steel or platinum. Corewire 22 is sufficiently stiff to restrain coil 13 in a straight configuration, despite the fact that the coil is biased to form a bent secondary shape. Clearly, coil 13 need not be restrained in a perfectly straight condition. In fact, a distal bend may be imposed on corewire 22 near the distal end 12 to facilitate intraluminal maneuvering. Additionally, the delivery system will preferably bend to follow the body lumen path during positioning. Jaws 18 will be permanently attached to body 16 by soldering, welding, adhesive bonding, or the like.

Coil 13 is released from body 16 by advancing release tube 20. The distal end of release tube 20 squeezes the jaws 18, thereby disengaging them from fitting 14. Release tube 20 generally comprises a high strength material having good column stiffness, preferably comprising a hypotube, a polyamide, or a tightly wound helical coil. Preferably, the distal end of release tube 20 fits within fitting 14 to ensure that the jaws are fully retracted. Optionally, a proximal actuation housing mechanically couples release tube 20 to the body 16 to facilitate release actuation (not shown).

Referring now to FIG. 2, coil 13 comprises an elongate resilient body formed as a primary coil 24. As described in copending U.S. patent application Ser. Nos. 08/474,779 and 08/475,252 (Attorney Docket Nos. 16355-24 and 16355-25), primary coil 24 is preferably formed as a straight coil on which a bent secondary shape is imposed. Coil 13 includes a distal loop 26, a proximal loop 28 and a generally straight lumen traversing region 30. Primary coil 24 generally comprises a wound resilient alloy wire, such as a stainless steel, platinum, or a shape memory alloy. To improve the effectiveness of coil 13 as an intrafallopian device, primary coil 13 preferably comprises an alloy of copper or copper plating.

Isthmus traversing region 30 includes a ribbon 32 wound over primary coil 24 to provide a helical outer shape. Ribbon 32 includes sharp outer edges 34 to further promote the retention of coil 13 within the fallopian tube. When used as an intrafallopian contraceptive device, the ribbon generally protrudes sufficiently to firmly engage the tubal wall, preferably having a width in the range between. 0.005 and 0.1 inch, a thickness in the range between. 0.001 and 0.2inch, and a pitch in the range between 0.01 and 0.2 inch. The overall contraceptive device geometry preferably facilitates introduction and retention, but is not large or rigid enough to interfere with internal tissue movements. Usually, the contraceptive device has a length in the range between 1.5 cm and 7.5 cm when in a relaxed state, while the distal loop and the proximal loop have outer diameters of at least 3 mm. Preferably, the primary coil has an outer diameter in the range between 0.2 mm and 5 mm.

Referring now to FIG. 3, alternative endoluminal coil delivery system 40 includes elongate body 16 and release tube 20, but no corewire 22 extends within the coil to restrain it in a straight configuration (see FIG. 1). Instead, a tubular structure 44 is slidably disposed over the coil. Coil 42 is released by advancing body 16 so that coil 42 extends from the distal end of tubular structure 44. Although coil 42 is not perfectly straight, tubular structure 44 restrains coil 42 within a diameter which allows axial insertion and positioning of the coil within the body lumen, and is therefore in a "straight configuration" as the term is used herein.

Figure 4B:
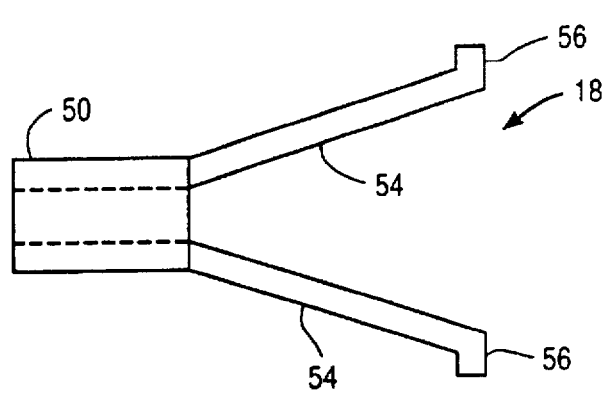
Figure 4C:
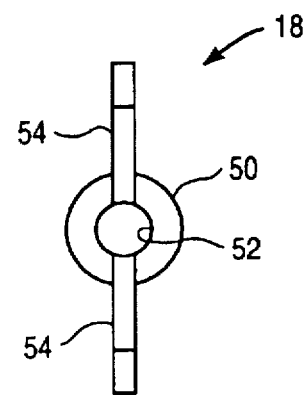

Referring now to FIGS. 4A–4C, jaws 18 generally comprise a collar 50 and a pair of tines 54. Collar 50 includes a central lumen 52 to facilitate the mounting of jaws 18 on elongate body 16. Tines 54 are cantilevered distally off collar 50 and carry pins 56 at their distal ends.

Jaws 18 are preferably formed as a unit from a high strength resilient alloy, ideally comprising stainless steel, platinum, or shape memory alloy. Tines 54 are resiliently biased outward, and are deflectable inward by release tube 20 (see FIGS. 1 and 3). optionally, a greater number of tines may be utilized, the tines generally being roughly evenly spaced about the axis of collar 50 so that the tines act in radial opposition. Alternatively, jaws 54 are biased inward and are held in an outward engaged position by the body prior to decoupling of the coil. Similarly, tines 54 could be designed to utilized inward facing pins to engage an external detent on a coil fitting. The exemplary embodiment is preferred, however, as it provides a particularly simple, compact, and fail-safe method for coupling elongate body 16 to the coil.

Figure 5A:
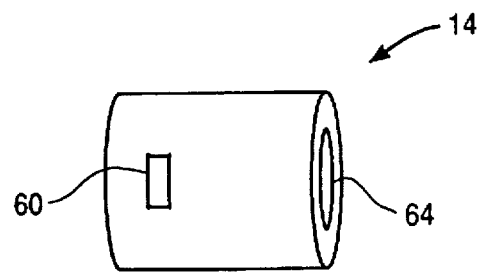
FIGS. 5A and 5B illustrate a coil fitting which meet with the jaws of FIGS. 4A-4C for use in the endoluminal delivery systems of FIGS. 1 and 3.
Figure 5B:
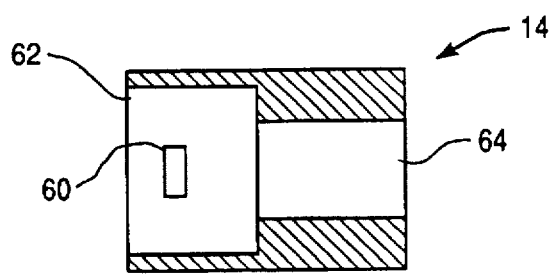

Referring now to FIGS. 5A and 5B, coil fitting 14 includes detents 60 which mate with pins 56 on jaws 18. Tines 54 expand outward from within a cavity 62, which in turn is in communication with a central passage 64. Central passage 64 provides access to the central lumen of the coil for coil wire 22 extending from body 16 (see FIG. 1).

Coil fitting 14 is generally soldered, welded, adhesively bonded, or molded over the proximal end of the endoluminal coil. Advantageously, coil fitting 14 provides a smooth, atraumatic outer surface, thereby reducing the risk of injury to the body lumen. Additionally, as detents 60 comprise passages through the cavity wall of coil fitting 14, they provide a visual safety check that the pins 56 of jaws 18 are securely engaged.

Although the exemplary embodiments have been described in detail, for clarity of understanding, a variety of modifications, variations, and alternatives may be practiced within the scope of the present invention. For example, the jaws may be carried by the coil, rather than the elongate body, while the associated fitting is attached to the delivery device. Alternatively, an endoscope or other optical visualization means may be combined with the present endoluminal coil delivery system, particularly for use as an intrafallopian contraceptive device, thereby providing a safe, highly effective, and inexpensive contraceptive method for women who have limited access to intensive care medical facilities. Therefore, the above description does not restrict the scope of the present invention, which is instead limited solely by the appended claims.

What is claimed is:

1. An endoluminal coil delivery system comprising:
   an endoluminal coil having a proximal end, a distal end, and a lumen extending from the proximal end toward the distal end;
   a first elongate body releasably attached proximal of the coil, wherein rotation of the first elongate body torques the coil;
   a corewire extending distally from the first elongate body, the corewire removably disposed within the lumen of the coil; and
   a second elongate body which articulates relative to the first body to remove the corewire from the lumen of the coil.

2. A delivery system as claimed in claim 1, wherein the corewire is capable of straightening the coil from within.

3. An endoluminal coil delivery system comprising:

an endoluminal coil having a proximal end, a distal end, and a lumen extending from the proximal end toward the distal end;

a first elongate body;

a corewire extending distally from the first elongate body, the corewire removably disposed within the lumen of the coil;

a second elongate body which articulates relative to the first body to remove the corewire from the lumen of the coil; and jaws affixed to the first elongate body, the jaws engaging the coil so that rotation of the first elongate body torques the coil, the jaws being disengageable from the coil by articulation of the second elongate body.

4. An endoluminal coil delivery system comprising:

an endoluminal coil having a proximal end, a distal end, and a lumen extending from the proximal end toward the distal end;

a first elongate body;

a corewire extending distally from the first elongate body, the corewire removably disposed within the lumen of the coil;

a second elongate body which articulates relative to the first body to remove the corewire from the lumen of the coil; and jaws affixed to the coil, the jaws engaging the first elongate body so that rotation of the first elongate body torques the coil, the jaws being disengageable from the first elongate body by articulation of the second elongate body.

5. An intrafallopian contraceptive delivery system comprising:

an intrafallopian coil having a proximal end, a distal end, a lumen therebetween, and an outer surface adapted for anchoring the coil in a fallopian tube;

a corewire removably disposed within the lumen of the coil;

a first elongate body extending proximally from the corewire to transcervically insert the coil into a fallopian tube and to engage the outer surface of the coil against a surrounding tubal wall; and a second elongate body which is actuatable relative to the first elongate body to remove the corewire from the lumen of the coil.

6. An intrafallopian contraceptive delivery system as claimed in claim 5, wherein the corewire is capable of straightening the coil from within.

7. An intrafallopian contraceptive delivery system as claimed in claim 5, wherein the coil comprises copper.

8. An intrafallopian contraceptive delivery system comprising:

an intrafallopian coil having a proximal end, a distal end, an axis therebetween, and an outer surface;

a corewire removably disposed within the lumen of the coil;

a first elongate body extending proximally from the corewire to transcervically insert the coil into a fallopian tube and to engage the outer surface of the coil against a surrounding tubal wall;

a second elongate body which is actuatable relative to the first elongate body to remove the corewire from the lumen of the coil; and jaws affixed to the first elongate body, the jaws engaging the coil so that rotation of the first elongate body torques the coil, the jaws being disengageable from the coil by articulation of the second elongate body.

9. An intrafallopian contraceptive delivery system comprising:

an intrafallopian coil having a proximal end, a distal end, an axis therebetween, and an outer surface;

a corewire removably disposed within the lumen of the coil;

a first elongate body extending proximally from the corewire to transcervically insert the coil into a fallopian tube and to engage the outer surface of the coil against a surrounding tubal wall;

a second elongate body which is actuatable relative to the first elongate body to remove the corewire from the lumen of the coil; and jaws affixed to the coil, the jaws engaging the first elongate body so that rotation of the first elongate body torques the coil, the jaws being disengageable from the first elongate body by articulation of the second elongate body.

10. A method for endoluminal placement of a coil, the method comprising:

inserting the coil into the body lumen;

anchoringly engaging an outer surface of the coil against a surrounding lumenal wall while a corewire supports the coil from within a lumen of the coil, wherein the coil is adapted for anchoring in the lumenal wall; and removing the corewire from the coil to release the coil within the body lumen.

11. A method as claimed in claim 10, wherein the coil is released while the outer surface engages the lumenal wall.

12. A method for endoluminal placement of a coil, the method comprising:

inserting the coil into the body lumen;

engaging an outer surface of the coil against a surrounding lumenal wall while a corewire supports the coil from within a lumen of the coil;

removing the corewire from the coil to release the coil within the body lumen; and manipulating jaws of a first elongate body to disengage the jaws from the coil, the first elongate body extending proximally from the corewire.

13. A method for endoluminal placement of a coil, the method comprising:

inserting the coil into the body lumen;

engaging an outer surface of the coil against a surrounding lumenal wall while a corewire supports the coil from within a lumen of the coil;

removing the corewire from the coil to release the coil within the body lumen; and manipulating jaws of the coil to disengage the jaws from a first elongate body, the first elongate body extending proximally from the corewire.

14. A method for placement of a contraceptive coil within a fallopian tube, the method comprising:

transcervically inserting the coil into the fallopian tube;

engaging an outer surface of the coil against a surrounding tubal wall; and removing a corewire from within a lumen of the coil to release the coil within the fallopian tube while the outer surface engages the tubal wall.

15. A method as claimed in claim 14, further comprising torquing the outer surface against the tubal wall to anchor the coil within the fallopian tube.

16. A method as claimed in claim 14, wherein the step of inserting the coil in the fallopian tube is carried out using a coil comprising copper.

17. A method for placement of a contraceptive coil within a fallopian tube, the method comprising:

transcervically inserting the coil into the fallopian tube;

engaging an outer surface of the coil against a surrounding tubal wall;

removing a corewire from within a lumen of the coil to release the coil within the fallopian tube while the outer surface engages the tubal wall; and articulating a second elongate body relative to a first elongate body to manipulate jaws so as to decouple the coil from the first elongate body, the first elongate body extending proximally from the corewire.

18. An endoluminal coil delivery system comprising:

an endoluminal coil having a lumen;

an elongate body;

means for releasably attaching the elongate body to the coil, such that rotation of the elongate body can torque the coil; and a corewire extending distally from the elongate body into the lumen of the coil.

19. A contraceptive delivery system for use in a fallopian tube, the system comprising:

a resilient intrafallopian coil having a distal end, a proximal end and a lumen therebetween;

an elongate body which is capable of advancing the coil into the fallopian tube;

a corewire extending distally from the elongate body into the lumen of the coil; and a mechanism which releasably couples the elongate body to the coil such that rotation of the elongate body can torque the coil while the coil is in a substantially straight configuration to anchor the coil against the surrounding fallopian tube.

20. A delivery system as claimed in claim 19, further comprising jaws affixed to the elongate body, the jaws engaging the coil, wherein the jaws are manipulated by a second elongate body to disengage the coil from the first body.

21. A delivery system as claimed in claim 19, further comprising jaws affixed to the coil, the jaws engaging the elongate body, wherein the jaws are manipulated by a second elongate body to disengage the coil from the first body.

22. A delivery system as claimed in claim 19, wherein the coil further comprises a helical ribbon wound over at least part of an outer surface of a primary coil.

23. A method for endoluminal placement of a coil, the method comprising:

inserting a coil into the body lumen;

engaging an outer surface of the coil against a surrounding lumenal wall;

torquing the coil against the surrounding lumenal wall by rotating an elongate body; and detaching the elongate body from the coils.

24. A method as claimed in claim 23, wherein the detaching step comprises manipulating jaws with a second elongate member so as to decouple the coil from the first elongate body.

25. A method as claimed in claim 23, further comprising removing a corewire from the lumen of the coil, so that the coil takes its relaxed shape.

26. A method for placement of a contraceptive coil within a tubal wall of a fallopian tube, the method comprising:

transcervically inserting a substantially straight coil into the fallopian tube;

torquing the substantially straight coil against a surrounding tubal wall;

disengaging the elongate body from the coil.

27. A method as claimed in claim 26, further comprising articulating a second body relative to the first body so as to decouple the coil from the first body.

28. A method as claimed in claim 26, further comprising removing a corewire from within the lumen of the coil to release the coil within the fallopian tube.

29. An endoluminal coil delivery system comprising:

an endoluminal coil having an outer surface;

a structure for anchoring the coil into a lumenal wall, wherein the structure is attached to the outer surface of the coil;

an elongate body having a proximal end and a distal end; and a mechanism on the elongate body for releasably attaching the coil to the elongate body, wherein the release mechanism is adapted to anchoringly engage the anchoring structure with the lumenal wall prior to releasing the coil.

* * * * *